United States Patent

Muth et al.

[11] Patent Number: 5,478,355
[45] Date of Patent: Dec. 26, 1995

[54] METHOD FOR IMPROVING THE IN VIVO STRENGTH RETENTION OF A BIOABSORBABLE IMPLANTABLE MEDICAL DEVICE AND RESULTING MEDICAL DEVICE

[75] Inventors: Ross R. Muth, Brookfield; Nagabhushanam Totakura; Cheng-Kung Liu, both of Norwalk, all of Conn.

[73] Assignee: United States Surgical Corporation, Norwalk, Conn.

[21] Appl. No.: 367,754

[22] Filed: Dec. 30, 1994

Related U.S. Application Data

[63] Continuation of Ser. No. 35,481, Mar. 18, 1993, abandoned.

[51] Int. Cl.⁶ .......................... A61B 17/04; C08G 63/70
[52] U.S. Cl. .................. 606/230; 523/113; 523/114; 523/115; 424/426
[58] Field of Search .................... 606/230, 231; 523/105, 113, 114, 115, 126; 424/426

[56] References Cited

U.S. PATENT DOCUMENTS

| | | | |
|---|---|---|---|
| 4,461,853 | 7/1984 | Gilead et al. | 523/126 |
| 4,496,446 | 1/1985 | Ritter et al. | 523/113 |
| 4,767,627 | 8/1988 | Caldwell et al. | 424/426 |
| 4,830,860 | 5/1989 | Ranade | 426/486 |
| 4,853,226 | 8/1989 | Machida et al. | 424/426 |
| 5,145,674 | 8/1992 | Lane et al. | 424/78.08 |
| 5,252,701 | 10/1993 | Jarrett et al. | 528/354 |

*Primary Examiner*—Gary Jackson

[57] ABSTRACT

A method is provided for improving the in vivo strength retention of a bioabsorbable implantable medical device such as a suture.

33 Claims, No Drawings

METHOD FOR IMPROVING THE IN VIVO STRENGTH RETENTION OF A BIOABSORBABLE IMPLANTABLE MEDICAL DEVICE AND RESULTING MEDICAL DEVICE

This is a continuation of U.S. application Ser. No. 08/035,481 filed Mar. 18, 1993, now abandoned.

BACKGROUND OF THE INVENTION

The present invention relates to a method for improving the in vivo strength retention of a bioabsorbable implantable medical device, e.g., a suture, staple, clip, pin, screw, ring, implant, prosthesis, etc., and to the resulting medical device. More particularly, the invention is directed to improving the in vivo strength retention of such a device by incorporating at least one basic metal compound into the bioabsorbable polymer from which the device is fabricated.

U.S. Pat No. 4,496,446 discloses a method of reducing the initial in vivo strength retention of surgical devices manufactured from polymers having a glycolic ester linkage by incorporating fillers such as barium sulfate, magnesium oxide, etc., into the polymers. The lowest disclosed level of use of filler was 12.5% in the case of barium sulfate-filled polyglycolic acid rods.

SUMMARY OF THE INVENTION

In accordance with the present invention, a method for improving the in vivo strength retention of a bioabsorbable implantable medical device is provided which comprises:

a) incorporating an in vivo strength retention-improving amount of at least one in vivo strength-retention improving, biocompatible basic metal compound substantially uniformly within the bioabsorbable polymer from which the medical device is to be formed; and, b) forming a medical device from the bioabsorbable polymer containing the basic metal compound, the medical device exhibiting appreciably greater in vivo strength retention compared to that of the same medical device formed from the bioabsorbable polymer into which no in vivo strength-retaining basic metal compound has been incorporated.

DESCRIPTION OF THE PREFERRED EMBODIMENTS

The bioabsorbable polymer into which the in vivo strength retention-improving basic metal compound is incorporated can be obtained by the polymerization of one or more bioabsorbable monomers such as glycolide, lactide, $\epsilon$-caprolactone, dioxanone, trimethylene carbonate, etc. Such polymers and methods for their preparation are well known, e.g., homopolymers and copolymers of glycolide and lactide as described in U.S. Pat. Nos. 2,703,316, 3,468,853, 3,636,956, 3,865,869 and 4,137,921; dioxanone homopolymers as described in U.S. Pat. Nos. 3,063,967, 3,063,968, 3,391,128, 3,645,941, 4,052,988 and 4,440,789; copolymers derived from dioxanone and at least one other monomer such as lactide, glycolide and caprolactone as described in U.S. Pat. Nos. 4,643,191, 4,653,497, 4,791,929, 4,838,267, 5,007,923, 5,047,048, 5,076,807, 5,080,665 and 5,100,433; homopolymers of trimethylene carbonate as described in U.S. Pat. Nos. 3,301,824, 3,379,693 and 4,920,203; copolymers derived from trimethylene carbonate and at least one other monomer such as lactide, glycolide, caprolactone and dioxanone as described in U.S. Pat. Nos. 4,891,263, 4,916,193, 4,920,203, 5,080,665 and 5,120,802; caprolactone homopolymers as described in U.S. Pat Nos. 2,878,236, 2,890,208, 3,021,309, 3,169,945, 3,190,858 and 3,284,417; copolymers derived from caprolactone and at least one other monomer such as lactide, glycolide, dioxanone and trimethylene carbonate as described in U.S. Pat. Nos. 4,605,730, 4,624,256, 4,700,704, 4,788,979, 4,791,929, 4,994,074, 5,076,807, 5,080,665, 5,085,629 and 5,100,433; and, copolymers derived from a polyalkylene oxide such as polyethylene glycol and at least one other monomer such as lactide, glycolide, dioxanone, trimethylene carbonate and caprolactone as described in U.S. Pat. Nos. 2,917,410, 4,452,973, 4,526,936, 4,624,256, 4,716,203, 4,857,602, 4,882,168, 5,019,094 and 5,123,912. In a preferred embodiment of the present invention, a glycolide-lactide copolymer is employed.

The biocompatible basic metal compounds which can be used to improve the in vivo strength retention characteristics of a bioabsorbable polymer in accordance with this invention include organic and inorganic compounds and their hydrates. Suitable basic organic metal compounds include sodium acetate, potassium acetate, sodium lactate, potassium lactate, calcium lactate, potassium glycolate, calcium glycolate, calcium propionate, calcium citrate, etc. Suitable basic inorganic metal compounds include the oxides, hydroxides, carbonates, phosphates and halides, e.g., calcium oxide, calcium hydroxide, calcium carbonate, calcium phosphate, calcium fluoride, magnesium oxide, magnesium hydroxide, magnesium carbonate, magnesium phosphate, sodium phosphate, sodium fluoride, potassium phosphate, potassium fluoride, and the like.

The amount of basic metal compound which is incorporated into the bioabsorbable polymer must be at least an in vivo strength retention-improving amount. In the present context, the expression "in vivo strength retention" refers to the ability of a medical device manufactured from a bioabsorbable polymer to retain its strength, e.g., the breaking load of the freshly manufactured medical device, after implantation of the medical device in the body.

In general, the incorporation of no more than about 0.5, and preferably no more than about 0.2, weight percent of basic metal compound into the polymer will provide significant improvement in the in vivo strength retention of the polymer. Thus, e.g., incorporation of from about 0.05 to about 0.25 weight percent of the basic metal compound into the bioabsorbable polymer is usually sufficient to increase the in vivo strength retention of the medical device formed therefrom by at least about 10 percent and will often provide increased strength retention levels of 20 percent or more. The use of amounts of basic metal compound much in excess of 0.5 weight percent should 5 ordinarily be avoided as they may interfere with the processability, e.g., extrudability, of the polymer or, as disclosed in U.S. Pat. No. 4,496,446 referred to above, such amounts may have the opposite effect of reducing the in vivo strength of the polymer and medical devices fabricated therefrom.

The basic metal compound should be evenly distributed within the bioabsorbable polymer employing any of the blending techniques which are known to be effective for achieving this. Thus, e.g., the basic metal compound can be substantially uniformly incorporated into the polymer by milling, melt blending, etc. Pellets or powders of the polymer can be coated with powders of the basic metal compound with blending occurring in the extruder which is employed in the subsequent processing of the polymer to provide a useful medical device.

The polymer of increased in vivo strength retention resulting from the method of the present invention can be employed in the fabrication of a wide variety of implantable medical devices such as surgical sutures, staples, clips, pins, screws, rings, implants, prostheses and the like. In the case of a surgical suture, the suture can be of monofilament or multifilament construction. The latter can be braided, twisted or spun using known and conventional techniques. For details of a preferred process of manufacturing a braided bioabsorbable suture, reference may be made to Kaplan et al. U.S. Pat. No. 5,019,093.

The following examples illustrate the improved in vitro strength retention properties of yarns manufactured from polymers having a basic metal compound incorporated therein.

EXAMPLE 1

The in vitro breaking loads of yarns produced from a 92.5:7.5 glycolide-lactide bioabsorbable copolymer having an inherent viscosity of 1.35 dl/g when measured in hexafluoroisopropyl alcohol at 30° C. and containing 0.1 weight percent of a basic metal compound substantially uniformly incorporated therein were measured. The yarns were made up of 27 filaments and were produced with 4.7 and 5.5 draw ratios. For purposes of comparison, the in vitro breaking load of a control yarn lacking a basic metal compound was also measured. Samples of the yarns were immersed for periods of time ranging from 1 to 3 weeks in an aqueous buffer solution maintained at a temperature of 37° C. to simulate the environment of the human body.

The yarns were removed and evaluated for strength retention by measuring their breaking load. Breaking load was measured by pulling the ends of a yarn in opposite directions using an Instron tester and measuring the amount of force required to break or sever the yarn. The breaking load measurements obtained herein are believed to correlate well with, and to be indicative of, the in vivo strength retention characteristics of the sutures.

The values for breaking load set forth in the following table are expressed in kilograms (kg) and as percentages of the original breaking load of the freshly extruded yarn prior to immersion in the buffer solution.

TABLE

IN VITRO BREAKING LOAD OF BIOABSORBABLE SUTURES

| Basic Metal Compound | Draw Ratio | Freshly Extruded Yarn | Yarn After 1 Week At 37° C. | % Initial Breaking Load Retained | Yarn After 2 Weeks At 37° C. | % Initial Breaking Load Retained | Yarn After 3 Weeks At 37° C. | % Initial Breaking Load Retained |
|---|---|---|---|---|---|---|---|---|
| Control | 5.5 | 7.94 | 6.46 | 92.4 | 5.68 | 72.4 | 1.97 | 23.9 |
| Magnesium oxide | 4.7 | 8.04 | 6.57 | 81.7 | 4.21 | 52.4 | 2.97 | 36.9 |
| Magnesium oxide | 5.5 | 8.08 | 7.64 | 94.6 | 5.00 | 61.9 | 2.68 | 33.2 |
| Magnesium hydroxide | 4.7 | 7.92 | 7.07 | 89.3 | 5.06 | 63.9 | 3.11 | 39.3 |

As these data show, the yarns containing an in vivo strength retention-increasing amount of basic metal compound in accordance with this invention exhibited significantly greater strength retention under equivalent simulated in vivo conditions than that of the control yarn specimen.

What is claimed is:

1. A method for improving the in vivo strength retention of a bioabsorbable implantable medical device which comprises:
   a) incorporating up to about 0.5 weight percent of at least one in vivo strength-retention improving, biocompatible, basic metal compound substantially uniformly within the bioabsorbable polymer from which the medical device is to be formed; and
   b) forming a medical device from the bioabsorbable polymer containing the basic metal compound, the medical device exhibiting about a 10 percent increase of in vivo strength retention compared to that of the same medical device formed from the bioabsorbable polymer to which no in vivo strength-retention improving basic metal compound has been incorporated.

2. The method of claim 1 wherein the basic metal compound is an organic compound.

3. The method of claim 1 wherein the basic metal compound is an inorganic compound.

4. The method of claim 1 wherein the basic metal compound is a metal oxide, metal hydroxide, metal carbonate, metal phosphate or metal halide.

5. The method of claim 1 wherein the basic metal compound is calcium oxide, calcium hydroxide, calcium carbonate, calcium phosphate, calcium fluoride, magnesium oxide, magnesium hydroxide, magnesium carbonate, magnesium phosphate, sodium phosphate, sodium fluoride, potassium phosphate and potassium fluoride.

6. The method of claim 1 wherein the basic metal compound is present in an amount less than about 0.2 weight percent of the bioabsorbable polymer.

7. The method of claim 1 wherein the in vivo strength retention of the bioabsorbable implantable medical device is increased by at least about 20 percent.

8. The method of claim 1 wherein the bioabsorbable polymer is derived from one or more monomers selected from the group consisting of glycolide, glycolic acid, lactide, lactic acid, ε-caprolactone, p-dioxanone and trimethylene carbonate.

9. The method of claim 1 wherein the medical device is selected from a group consisting of a surgical suture, staple, clip, pin, screw, ring, implant and prosthetic device.

10. The method of claim 1 wherein the bioabsorbable polymer is a copolymer derived from glycolide and lactide and the medical device is a surgical suture.

11. A polymeric bioabsorbable surgical suture containing an in vivo strength retention-improving amount of up to about 0.5 weight percent of at least one in vivo strength-retaining biocompatible basic metal compound which is substantially uniformly incorporated within the bioabsorbable polymer from which the surgical suture is made.

12. The bioabsorbable surgical suture of claim 11 wherein the basic metal compound is an organic compound.

13. The bioabsorbable surgical suture of claim 11 wherein the basic metal compound is an inorganic compound.

14. The bioabsorbable surgical suture of claim 11 wherein the basic metal compound is a metal oxide, metal hydroxide, metal carbonate, metal phosphate or metal halide.

15. The bioabsorbable surgical suture of claim 11 wherein the basic metal compound is calcium oxide, calcium hydroxide, calcium carbonate, calcium phosphate, calcium fluoride, magnesium oxide, magnesium hydroxide, magnesium carbonate, magnesium phosphate, sodium phosphate, sodium fluoride, potassium phosphate and potassium fluoride.

16. The bioabsorbable surgical suture of claim 11 wherein the basic metal compound is present in an amount less than about 0.2 weight percent of the bioabsorbable polymer.

17. The bioabsorbable surgical suture of claim 11 which is of braided construction.

18. The bioabsorbable surgical suture of claim 11 wherein the in vivo strength retention of the suture is improved by at least about 10 percent.

19. The bioabsorbable surgical suture of claim 11 wherein the in vivo strength retention of the suture is improved by at least about 20 percent.

20. The bioabsorbable surgical suture of claim 11 wherein the bioabsorbable polymer from which the suture is made is derived from one or more monomers selected from the group consisting of glycolide, glycolic acid, lactide, lactic acid, ε-caprolactone, p-dioxanone and trimethylene carbonate.

21. The bioabsorbable surgical suture of claim 11 containing from about 0.05 to about 0.25 weight percent of in vivo strength retention-improving basic metal compound to increase the in vivo strength retention of the suture by at least about 10 percent.

22. The bioabsorbable surgical suture of claim 21 which is of braided construction and wherein the bioabsorbable polymer from which the suture is made is derived from one or more monomers selected from the group consisting of glycolide, glycolic acid, lactide, lactic acid, ε-caprolactone, p-dioxanone and trimethylene carbonate.

23. The bioabsorbable surgical suture of claim 21 wherein the basic metal compound is a metal oxide, metal hydroxide, metal carbonate, metal phosphate or metal halide.

24. The bioabsorbable surgical suture of claim 21 wherein the basic metal compound is calcium oxide, calcium hydroxide, calcium carbonate, calcium phosphate, calcium fluoride, magnesium oxide, magnesium hydroxide, magnesium carbonate, magnesium phosphate, sodium phosphate, sodium fluoride, potassium phosphate and potassium fluoride.

25. A bioabsorbable polymer containing an in vivo strength retention-improving amount of up to about 0.5 weight percent of at least one in vivo strength-retaining biocompatible basic metal compound which is substantially uniformly incorporated within the bioabsorbable polymer from which the surgical suture is made.

26. The bioabsorbable polymer of claim 25 wherein the basic metal compound is an organic compound.

27. The bioabsorbable polymer of claim 25 wherein the basic metal compound is an inorganic compound.

28. The bioabsorbable polymer of claim 25 wherein the basic metal compound is a metal oxide, metal hydroxide, metal carbonate, metal phosphate or metal halide.

29. The bioabsorbable polymer of claim 25 wherein the basic metal compound is calcium oxide, calcium hydroxide, calcium carbonate, calcium phosphate, calcium fluoride, magnesium oxide, magnesium hydroxide, magnesium carbonate, magnesium phosphate, sodium phosphate, sodium fluoride, potassium phosphate and potassium fluoride.

30. The bioabsorbable polymer of claim 25 wherein the basic metal compound is present in an amount less than about 0.2 weight percent of the bioabsorbable polymer.

31. The bioabsorbable polymer of claim 25 wherein the in vivo strength retention of the suture is improved by at least about 10 percent.

32. The bioabsorbable polymer of claim 25 wherein the in vivo strength retention of the suture is improved by at least about 20 percent.

33. The bioabsorbable polymer of claim 25 wherein the bioabsorbable polymer from which the suture is made is derived from one or more monomers selected from the group consisting of glycolide, glycolic acid, lactide, lactic acid, ε-caprolactone, p-dioxanone and trimethylene carbonate.

* * * * *